(12) United States Patent
Igarashi (10) Patent No.: US 6,632,172 B1
(45) Date of Patent: Oct. 14, 2003

(54) ENDOSCOPE APPARATUS

(75) Inventor: Haruko Igarashi, Hachioji (JP)

(73) Assignee: Olympus Optical Co., Ltd., Tokyo (JP)

( * ) Notice: Subject to any disclaimer, the term of this patent is extended or adjusted under 35 U.S.C. 154(b) by 169 days.

(21) Appl. No.: 09/714,489

(22) Filed: Nov. 17, 2000

(51) Int. Cl.[7] ................................................. A61B 1/06
(52) U.S. Cl. ..................... 600/166; 600/160; 600/101
(58) Field of Search ............................ 600/166, 111, 600/176, 160, 101; 348/45; 359/377, 378

(56) References Cited

U.S. PATENT DOCUMENTS

| | | | | |
|---|---|---|---|---|
| 5,522,789 A | * | 6/1996 | Takahashi | 600/166 |
| 5,776,049 A | * | 7/1998 | Takahashi | 600/111 |
| 5,971,915 A | * | 10/1999 | Yamamoto et al. | 600/111 |
| 6,104,426 A | * | 8/2000 | Street | 348/45 |
| 6,327,079 B1 | * | 12/2001 | Namii et al. | 359/376 |
| 2001/0012053 A1 | * | 8/2001 | Nakamura | 348/45 |

* cited by examiner

*Primary Examiner*—Henry Bennett
*Assistant Examiner*—Nihir Patel
(74) *Attorney, Agent, or Firm*—Armstrong, Westerman & Hattori, LLP

(57) ABSTRACT

An endoscope apparatus having an insertion part which includes an object optical system in order to conduct measurements or stereoscopic-vision observations, using the object optical system with a moderate parallax, a moderate size of an image can be provided without making an endoscope thick in diameter.

6 Claims, 8 Drawing Sheets

ENDOSCOPE APPARATUS

FIELD OF THE INVENTION

This invention relates to an endoscope apparatus with an insertion part having a small outer diameter which includes an object optical system to conduct measurements or stereoscopic-vision observations.

BACKGROUND OF THE INVENTION

Conventionally, an endoscope which includes a long and thin insertion part which is inserted into a cavity or the intra-corporeal of a human being for observation, etc., has been widely used in both the industrial field and the medical field. Furthermore in recent years, there have been a great need to measure the size and the depth of flaws and cracks in the industrial field, and to perform surgery using an endoscope in the medical field. Moreover in the medical field, using stereo images to recognize depth information is well known.

Figure 6:
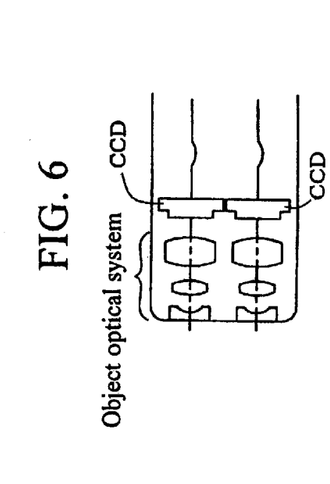
FIG. 6 illustrates a conventional object optical system of an endoscope which enables stereoscopic vision.

A conventional endoscope in which stereo observation are possible is described in Japanese Laid-open Patent Publication No. 8-29701. As shown in FIG. 6, two objective-lens systems are arranged in parallel and at the end of an endoscope insertion part. The endoscope conducts parallax stereoscopic vision by receiving an image from two image-pick-up devices (henceforth, CCD) and shifting the image due to the positional differences of the two CCDs.

In the optical system with two CCDs, since the number of pixels can be increased as compared to one CCD, it is effective in improving the image quality of stereo images and the precision of measurements. However, by arranging two CCDs in parallel, it then becomes difficult to reduce the size of an endoscope which makes it difficult to observe a narrow site or perform minimum invasive surgery.

Figure 7:
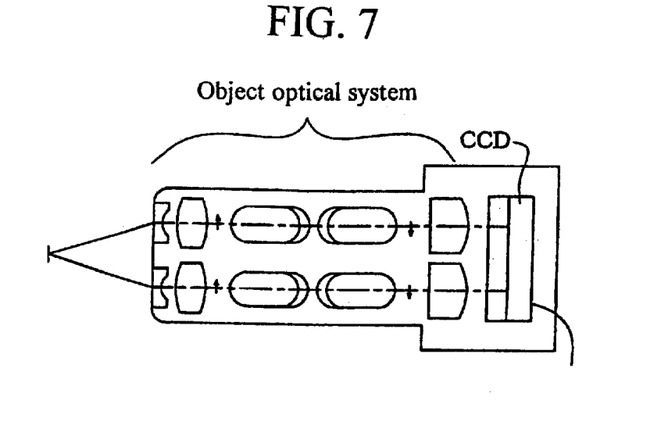
FIG. 7 illustrates a second conventional object optical system of an endoscope which enables stereoscopic vision.

A conventional endoscope having an optical system in which an image with a parallax is formed on one CCD is described in Japanese Laid-open Patent Publication No. 7-35989. As shown in FIG. 7, this optical system has one CCD on the extension line of the respective optical axis of the two object optical systems arranged in parallel to form two images. The distance between the two optical axes is hereinafter referred to as "the optic-axial distance".

Figure 8:
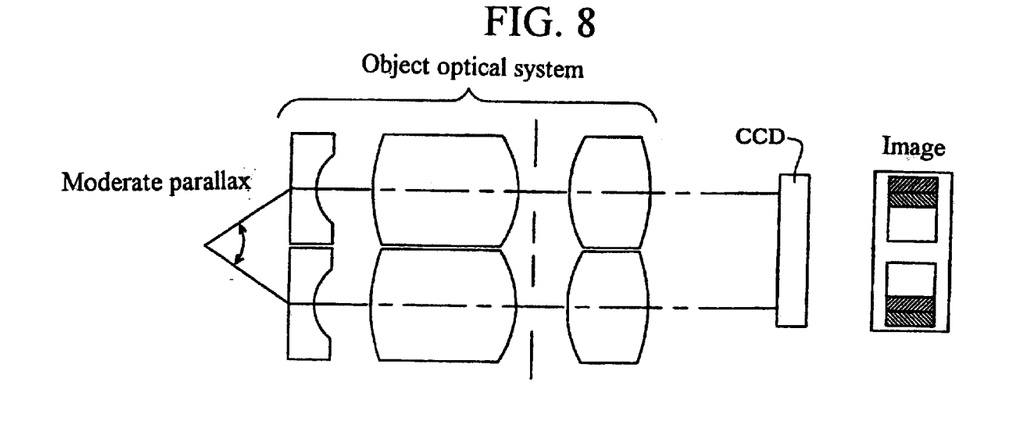
FIG. 8 illustrates that the center of an image will be positioned at the end of the CCD, if the CCD is small for the second conventional system shown in FIG. 7.

On the one hand, in recent years the trend has been toward smaller-sized CCDs. However, if the optimum optic-axial distance is determined such that a part of the object optical system nearest to the object has a moderate parallax, and an image is formed on the CCD with that optic-axial distance, as shown in FIG. 8, the center of an image will be positioned at the end of the CCD, if the CCD is small. That is, the area of the images at the right and left sides of the CCD, marked with diagonal lines in FIG. 8, decreases and causes interference with the stereoscopic vision and measurements.

Figure 9:
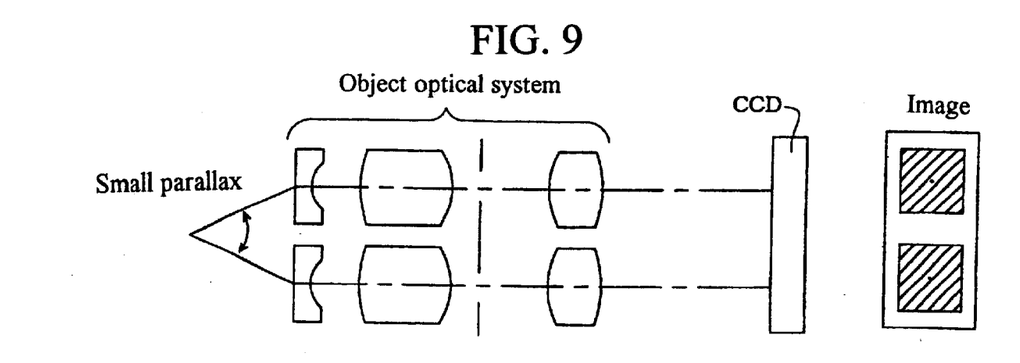
FIG. 9 illustrates a possibility that a parallax required for a measurement or for stereoscopic vision cannot be obtained for the second conventional system shown in FIG. 7.

Conversely, if the size of the CCD to be used and the optimum distance between the centers of the images on the CCD is also determined in accordance with the size of an endoscope, as shown in FIG. 9, there is a possibility that a parallax required for a measurement or for stereoscopic vision cannot be obtained if the optic-axial distance for the object optical system on the object side (nearest the object) is equal to the distance between the centers of the images on the CCD.

Therefore, in order to obtain a moderate parallax required for a measurement or a stereoscopic vision as well as an acceptable image on the CCD, the optic-axial distance of an object optical system, and the distance between the centers of the images on CCD need to be varied.

However, the optic-axial distance of an object optical system influences a parallax which is important at the time of a stereoscopic-vision observation and the precision at the time of measurement. If the optic-axial distance of the object optical system nearest to the object is narrow, a parallax will decrease so that depth information becomes hard to obtain when carrying out a stereoscopic vision and a measurement error becomes large when carrying out a measurement operation.

Conversely, if the optic-axial distance of the object optical system nearest to the object is wide, a parallax will become large. Although the precision of a measurement improves, the problem will arise that the end of an endoscope becomes large. And since a parallax is too large when carrying out a stereoscopic-vision observation, it is hard to observe on the contrary.

A parallax depends not only on the optic-axial distance of the object optical system nearest to the object but also on the distance to the object to be observed. In other words, the closer the object is, the larger the parallax becomes, and the farther it is, the smaller the parallax becomes.

Based on the above, in order to obtain a moderate parallax required for measurement and for a stereoscopic-vision observation depending on the observation distance, and in order not to make the size of an endoscope large, the optic-axial distance of the object optical system at a part thereof nearest to the object should be determined.

A conventional example in which the optic-axial distance of an object optical system is different from the distance between the centers of the images on the CCD is described in the Japanese Laid-open Patent Publication No. 62-215221.

Figure 10:
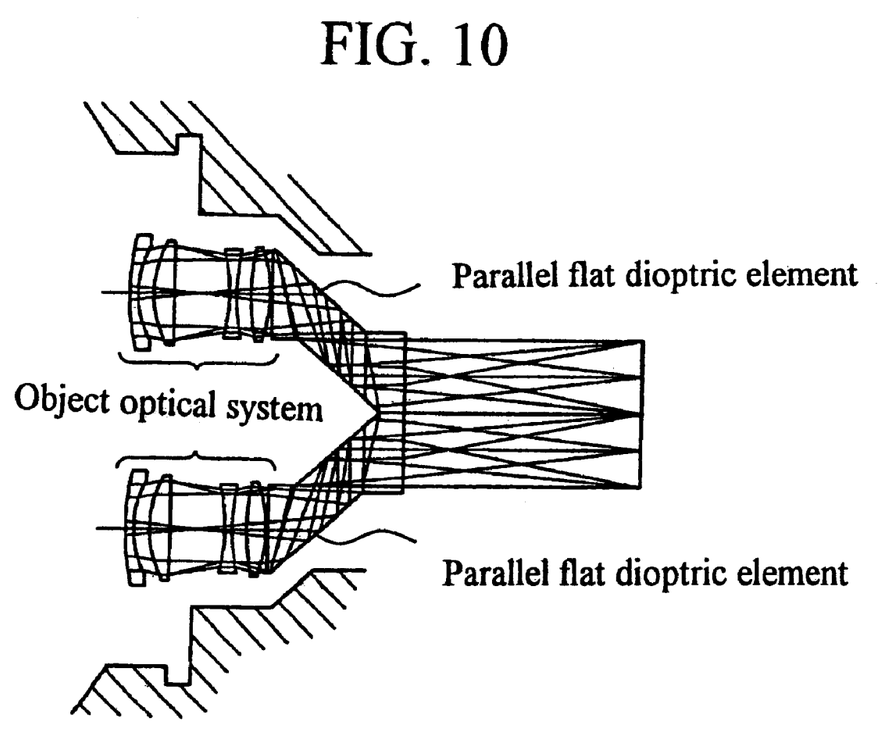
FIG. 10 illustrates a third conventional system that sandwiches a parallel flat dioptric element with a pair of optical systems.

In this example, as shown in FIG. 10, by sandwiching a parallel flat refractive element with a pair of optical systems, the optic-axial distance of an object optical system is narrowed towards the center of the image on the CCD. In such an optical system, if the CCD is small, the parallel flat dioptric element must be small. However, it is difficult to design and manufacture a small parallel flat dioptric element, and still more difficult to sandwich it with a pair of optical systems.

SUMMARY OF THE INVENTION

It is an object of the present invention to provide an object optical system with a moderate parallax and a moderate image size, without making the insertion part of the endoscope thick in diameter.

Figure 1:
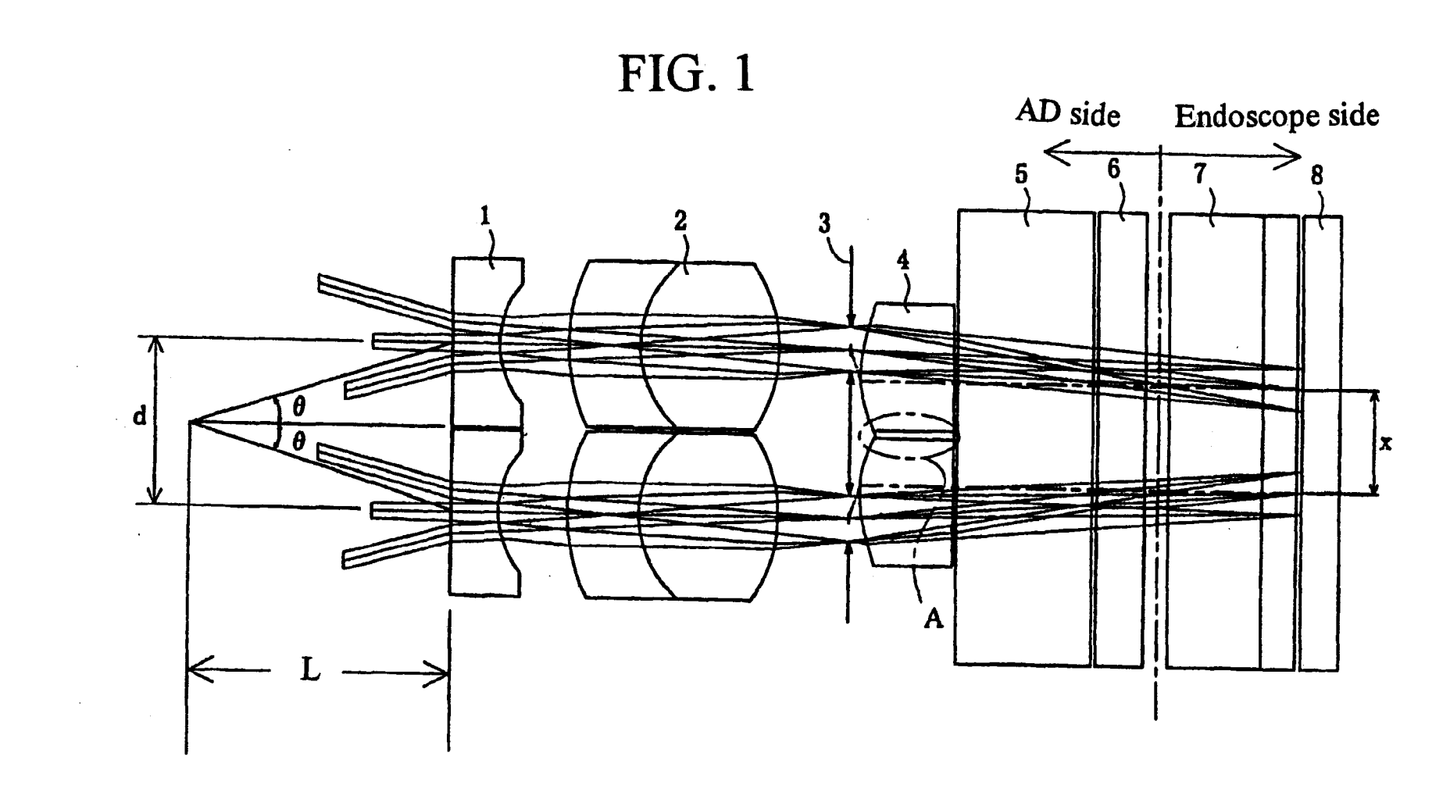
FIG. 1 illustrates an object optical system according to a first example of the present invention.

In an endoscope apparatus, according to the present invention, equipped with an object optical system to conduct a measurement or a stereoscopic-vision observation, as shown in FIG. 1, the object optical system comprises a pair of negative lenses; a first pair of positive-lenses; a brightness diaphragm; a second pair of positive-lenses; and an image-pick-up device for forming an object image. These elements are arranged in order from an object side. A pair of optical axes are defined by the pair of negative lenses, the first pair of positive-lenses and the brightness diaphragm. The second pair of positive-lenses are arranged eccentrically with respect to the pair of optical axes in a direction towards each other.

Each lens of the second pair of positive-lenses can be defined as a single-lens, plural single-lenses, or cemented lens or combination thereof.

The eccentric lenses may be provided on only one side of the second pair of positive-lenses, or on a part of the second pair of positive-lenses. It is noted that the centers, of the positive-lenses of the second pair, is the center of the circle if the lens shape is a circle, and it is the center of gravity of a polygon if the lens shape is a polygon.

The endoscope apparatus according to this invention, wherein the following conditional expression is satisfied:

$$0.2 \leq x/d \leq 0.9 \quad (1)$$

wherein x represents an optic-axial distance of said pair of optical axes on the image-pick-up device side, and d represents the optic-axial distance of said pair of optical axes of the object side, the brightness diaphragm, respectively.

The positive-lenses of the second pair are arranged eccentrically with respect to a pair of optical axes in a direction in which the lenses come closer to each other symmetrically and by the same amount. According to this invention, the second pair of positive-lenses on the image-pick-up device side from a brightness diaphragm is arranged to be inwardly eccentric, with respect to each optical axis on the object side from a brightness diaphragm, towards the horizontal direction of the CCD surface.

The amount of the eccentricity of the second pair of positive-lenses does not necessarily need to be symmetrical. In a stereoscopic-vision endoscope, however, it is important to minimize the aberrational difference of the left and right images. It is preferable that the left and right images are balanced by making the eccentricity symmetric.

Moreover, each of the positive-lenses of the second pair has a cutout portion at the peripheral thereof where the two lenses abut so that the centers of the positive-lenses come closer to each other. Specifically, the distance between the centers of circumferences of the positive-lenses is less than the sum of radii thereof. It is preferable that the shape of the cutout portion be a straight line which is easy to process.

Figure 4:
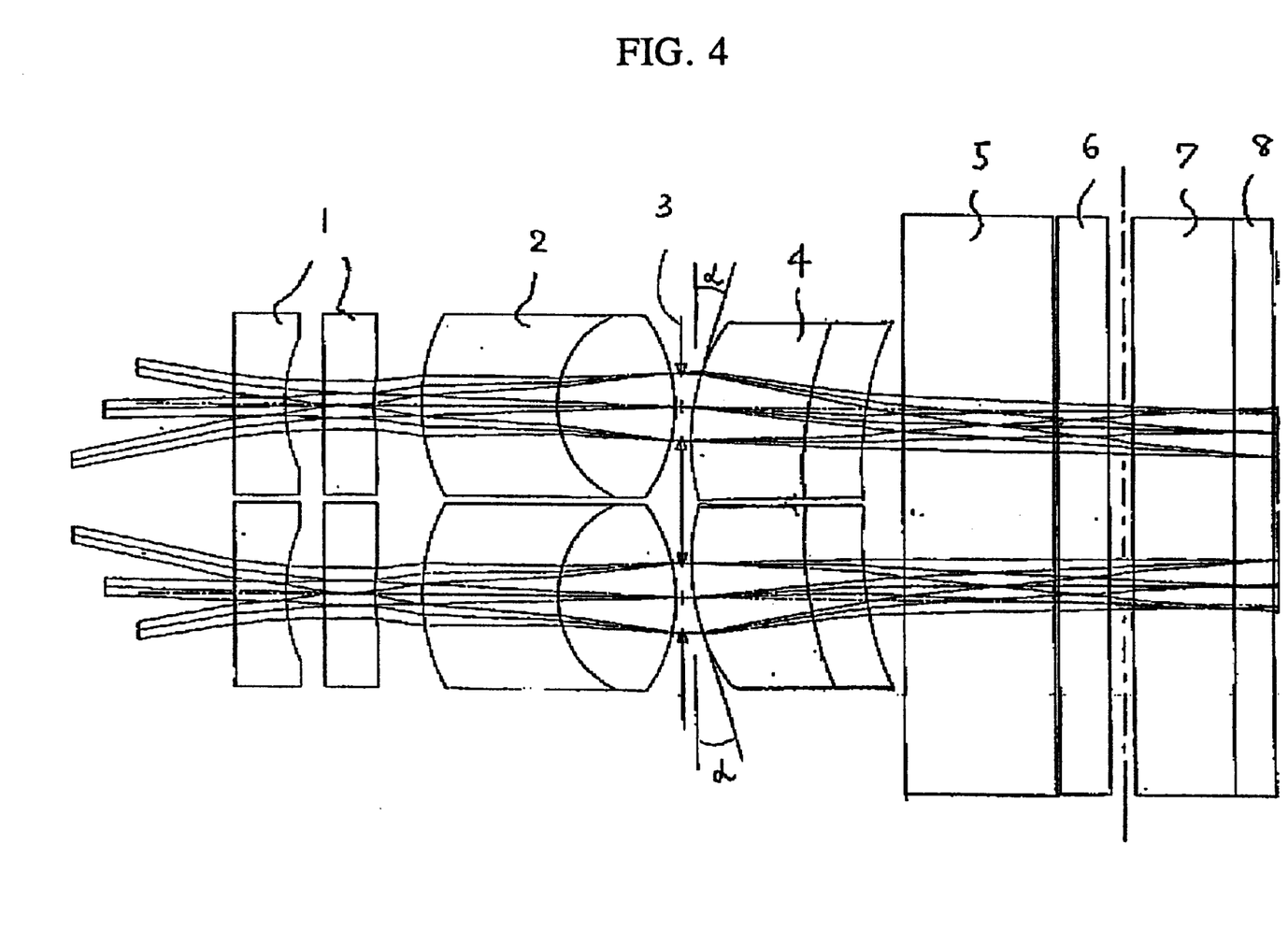
FIG. 4 illustrates an object optical system according to a third example of the present invention..

The positive-lenses of the second pair are arranged to tile eccentrically by angle a, as shown in FIG. 4, in a manner that each optical axis includes inwardly from the object side toward the image side symmetrically and by the same amount.

The amount of eccentricity of the second pair of positive-lenses does not necessarily need to be symmetrical. In a stereoscopic-vision endoscope, however, it is important to minimize the aberrational difference of the left and right images. It is preferable that the left and right images are balance by making the eccentricity symmetric.

Moreover, each of the positive-lenses of the second pair has a cutout portion at the peripheral thereof where the two lenses abut so that the centers of the positive-lenses come closer to each other. Specifically, the distance between the centers of circumferences of the positive-lenses is less than the sum of radii thereof. It is preferable that the shape of the cutout portion be a straight line which is easy to process.

According to this invention, it is constituted so that the following conditional-expression (2) may be satisfied:

$$0.03L < d < 2L \quad (2)$$

wherein d represents the optic-axial distance of said pair of optical axes at the object side, and L represents the best observation distance of said object optical system.

The minimum of this equation is necessary a condition in order to obtain a parallax and furthermore obtain precision required at the time of measurement. As illustrated in FIG. 1, when setting the best observation distance at L, it is considered that 1 degree more is required for an convergence angle (θ). The best observation distance herein implies a distance to the object which is most suitable for the observation. In the case of an endoscope, it is usually about 5–100 mm. If the convergence angle (θ) is 1 degree or less, a parallax will decrease and it becomes hard to obtain information on the depth direction when carrying out the stereoscopic vision. Moreover, in that case, a measurement error becomes large when measuring an objective shape.

The value of the upper limit of the above formula (2) not only restrains the size of an end portion of the endoscope from becoming large, but also prevents the observation from becoming difficult to observe because of a too large parallax.

According to this invention, the end adapter is detachable from the image-pick-up device.

As illustrated in FIG. 1, an end adapter system which includes the pair of negative lenses, the first pair of positive lenses, the brightness diaphragm and the second pair of positive lenses is detachable in the direction of an arrow at the chain-line position. The rear part is the endoscope side part containing a cover glass 7 and an image-pick-up device 8. Accordingly, the angle of view of the endoscope, the viewing angle, and the convergence angle which influences a parallax are arbitrarily exchangeable by replacing the adapter part.

Figure 3:
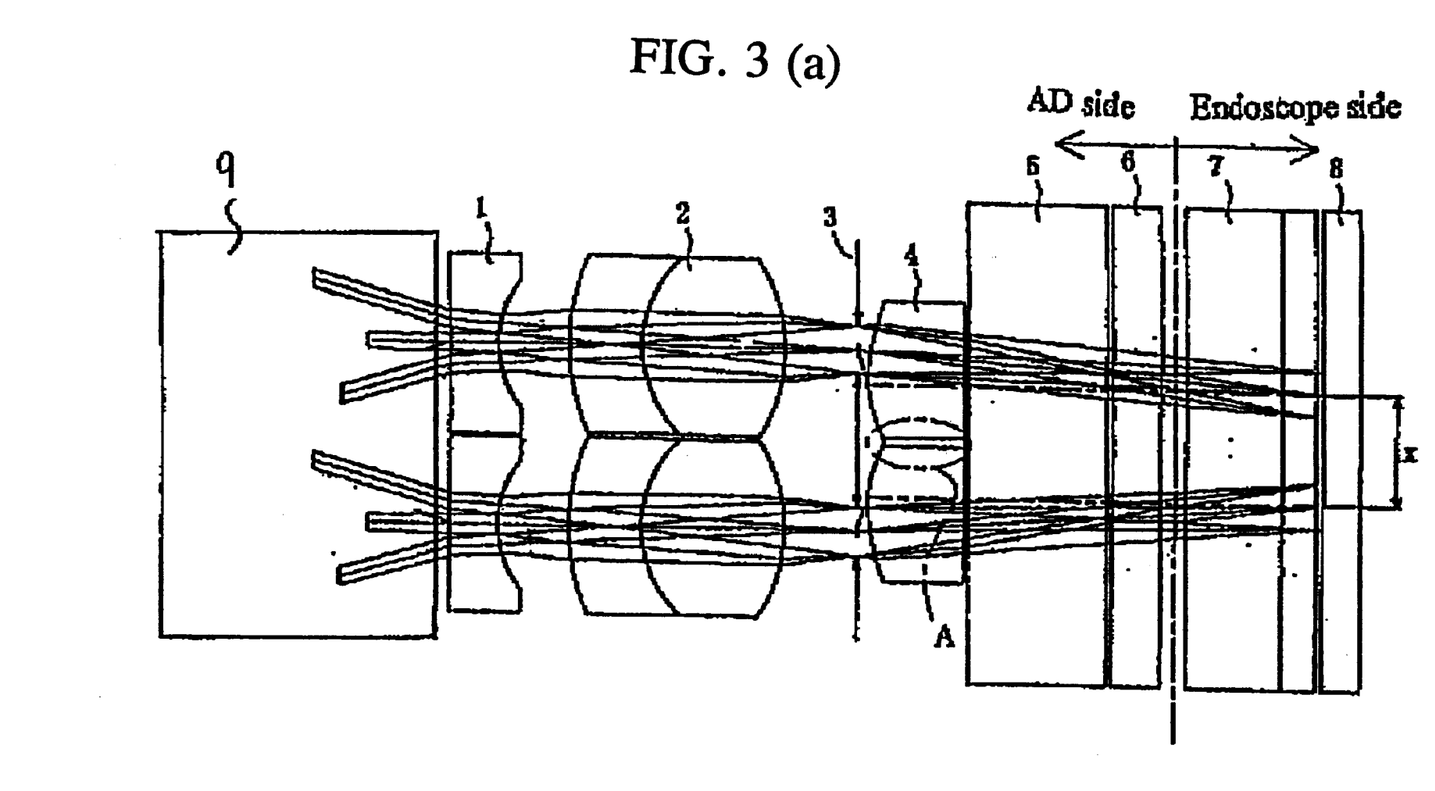
FIG. 3(a) illustrates an object optical system according to a second example of the present invention.
FIG. 3(b) illustrates a side view of the object optical system shown in FIG. 3(a).

According to this invention, a prism for covering the line of sight is arranged between an object and the pair of negative lenses, as shown in FIG. 3(b) (side view of FIG. 3(a)). As apparent from FIGS. 3(a) and 3(b), at least one prism for converting the line of sight 10, a pair of negative lenses 1, a first pair of positive-lenses 2, a brightness diaphragm 3, the second pair of positive-lenses 4, and an image-pick-up device 8 are provided in order from the object side. The second pair of positive-lenses are eccentric with respect to each of the optical axis on the object side from the brightness diaphragm. With this structure, the angle of view is determined by the pair of negative lenses and the first pair of positive-lenses on the object side from the brightness diaphragm. Simultaneously, aberrations, such as a spherical-aberration and curvature of field, are restrained as well. And, by shifting the optical axes of the second pair or positive lenses after reducing a diameter of a luminous flux through the brightness diaphragm, the aberrational influence by eccentricity is decreased. Free selection of the line of sight is effective is observing a narrow space.

According to an embodiment of this invention, an effective image-pick-up range of the image-pick-up device is 2 to 2.5 mm or less.

Figure 5:
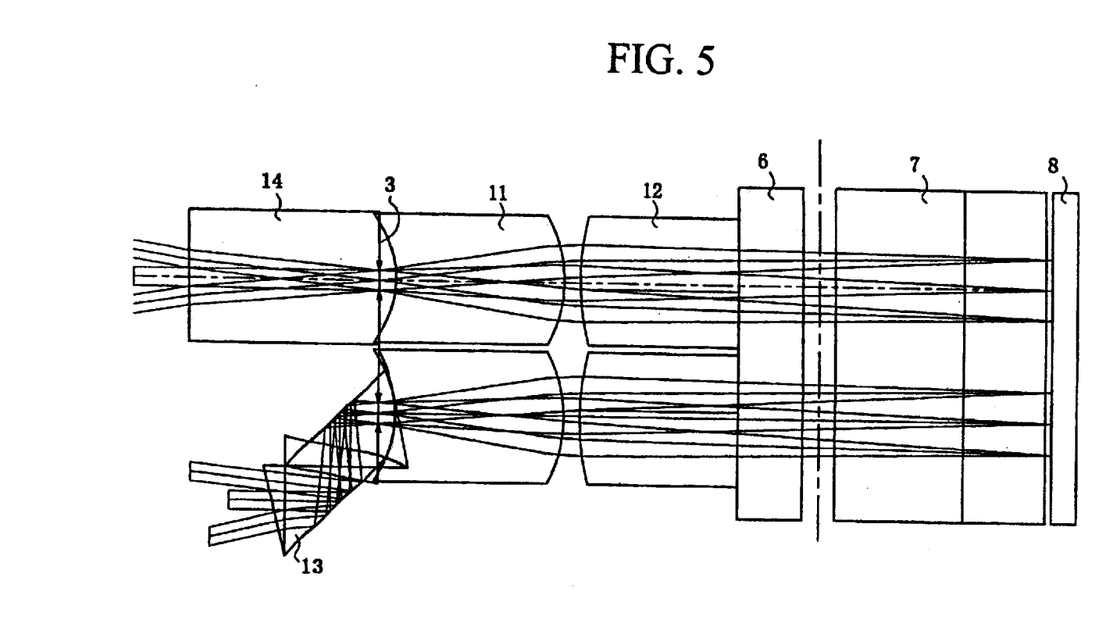
FIG. 5 illustrates an object optical system according to a fourth example of the present invention.

In the object optical system of the endoscope according to the present invention, as shown in FIG. 5, the object optical system comprises a brightness diaphragm 3, a pair of positive-lenses 11, 12 and an image-pick-up device 8 for forming an object image. These elements are arranged in order from the object side. An optic-axially eccentric device 13 is arranged adjacent the brightness diaphragm 3, and the optic-axial distance on the object side determined by the optic-axially eccentric device 13 is eccentric with respect to the optic-axial distance determined by a pair of positive-lenses 11, 12 on the image side from the brightness diaphragm.

Moreover, according to this invention, the following conditional-expression (1) is satisfied:

$$0.2 \leq x/d \leq 0.9 \quad (1)$$

wherein x represents an optic-axial distance of a pair of optical axes on the side of the image-pick-up device from the brightness diaphragm, and d represents the optic-axial distance of the pair of optical axes on the side of an object from the brightness diaphragm.

The optic-axially eccentric device is disposed within 0.5 mm from the brightness diaphragm. The reason why the optic-axially eccentric device is provided adjacent to the brightness diaphragm is that the size of the optic-axially device becomes small if the amount of eccentricity becomes comparatively small when using a small-sized image pick-up device. Therefore, it is desirable to arrange it adjacent to the brightness diaphragm with a low light height.

The term "adjacent the brightness diaphragm" herein implies not only that the optic-axially eccentric device is disposed within 0.5 mm from the brightness diaphragm, but also that the brightness diaphragm can be disposed within the optic-axially eccentric device. In this embodiment, it is preferable that the small image-pick-up device have an effective image-pick-up range of 2 to 2.5 mm or less.

In this constitution, it is more desirable to provide the optic-axially eccentric device on one of the optical systems which shifts the optical axis in a horizontal direction of the CCD image surface. This is because, in the endoscope of a narrow diameter, if two optical elements which make the optical axes eccentric are used, like a prior art example, each optical element should be made small and a manufacture process becomes much more difficult.

According to another embodiment, the optic-axially eccentric device has a prism with two reflecting surfaces, or two reflective mirrors.

According to this invention, the following conditional expression is satisfied:

$$0.03L < d < 2L \quad (2)$$

wherein d represents the optic-axial distance of a pair of optical axes on the object side from said brightness diaphragm, and L represents the best observation distance of the object optical system.

Preferably, the end adapter is detachable from the image-pick-up device. Preferably, the effective image pick-up-range of the image pick-up-device is 2 to 2.5 mm or less.

DETAILED DESCRIPTION OF THE PREFERRED EMBODIMENT

With reference to the accompanying drawings, examples of object optical systems illustrating the embodiments of the present invention, will be described hereinafter.

In the following examples, same elements of the object optical systems are identified by the same reference numerals.

FIG. 1 illustrates an object optical system according to a first example of the present invention. In this example, the object optical system includes a pair of negative lenses 1, a first pair of positive-lenses 2, a brightness diaphragm 3, a second pair of positive-lenses 4, infrared cut off filter 5, cover glasses 6, 7, an image-pick-up device 8, in order from an object side.

The second pair of positive-lenses 4 are eccentric to the respective optical axis from the object side to the brightness diaphragm 3. In addition, a pair of negative lenses 1 are plane-concave lens with the concave surface oriented to the image-surface side. A first pair of positive-lenses 2, behind the negative lens 1, consists of a concave-convex doublet.

The brightness diaphragm 3 consists of two apertures. Moreover, the second pair of positive-lenses 4 consist of respective plano-convex lens which are eccentric to each optical axis on the object side, from the brightness diaphragm 3, in the screen horizontal direction, eccentric by in the same amount, respectively, and the convex surface are oriented to the object side. The center part shown by symbol A is cut out so that each lens does not interfere with the other.

The infrared cut off filter 5 in common in the left and right optical systems, the cover glass 6, 7 and the image-pick-up device 8 are arranged behind the lens. This Example has the structure of an end adapter system detachable in the direction of an arrow at the chain-line position.

The rear part of the endoscope includes a cover glass 7 and an image-pick-up device 8. Accordingly, it is possible to change arbitrarily the angle of view of the viewing angle of an endoscope, and the convergence angle which influences a parallax by replacing an adapter part.

The value corresponding to each above-mentioned conditional expression and lens data are as follows.

x=0.986 d=1.599
L=13.69
0.2≦x/d=0.62≦0.9
0.03L<d=0.12L<2L
Object distance 13.6896

| | | | |
|---|---|---|---|
| r1 = infinity | d1 = 0.04381 | n1 = 1.88300 | v1 = 40.78 |
| r2 = 0.8436 | d2 = 0.2409 | | |
| r3 = infinity | d3 = 0.4275 | | |
| r4 = 1.9713 | d4 = 0.6727 | n4 = 1.84666 | v4 = 23.78 |
| r5 = 0.9857 | d5 = 1.3142 | n5 = 1.51633 | v5 = 64.14 |
| r6 = −1.3015 | d6 = 0.7051 | | |
| r7 = infinity(diaphragm) | d7 = 0.1095 | | |
| r8 = 2.2431 | d8 = 0.8785 | n8 = 1.78800 | v8 = 47.37 |
| r9 = infinity | d9 = 0.0329 | | |
| r10 = infinity | d10 = 1.3142 | n10 = 1.51400 | v10 = 75.00 |
| r11 = infinity | d11 = 0.0329 | | |
| r12 = infinity | d12 = 0.4381 | n12 = 1.88300 | v12 = 40.76 |
| r13 = infinity | d13 = 0.2190 | | |
| r14 = infinity | d14 = 0.8761 | n14 = 1.88300 | v14 = 40.76 |
| r15 = infinity | d15 = 0.3286 | n15 = 1.49700 | v15 = 81.61 |
| r16 = infinity | d16 = 0.0329 | | |
| r17 = infinity | | | |

The eccentricity of each convex lens 4=0.3356 horizontally.

Figure 2:
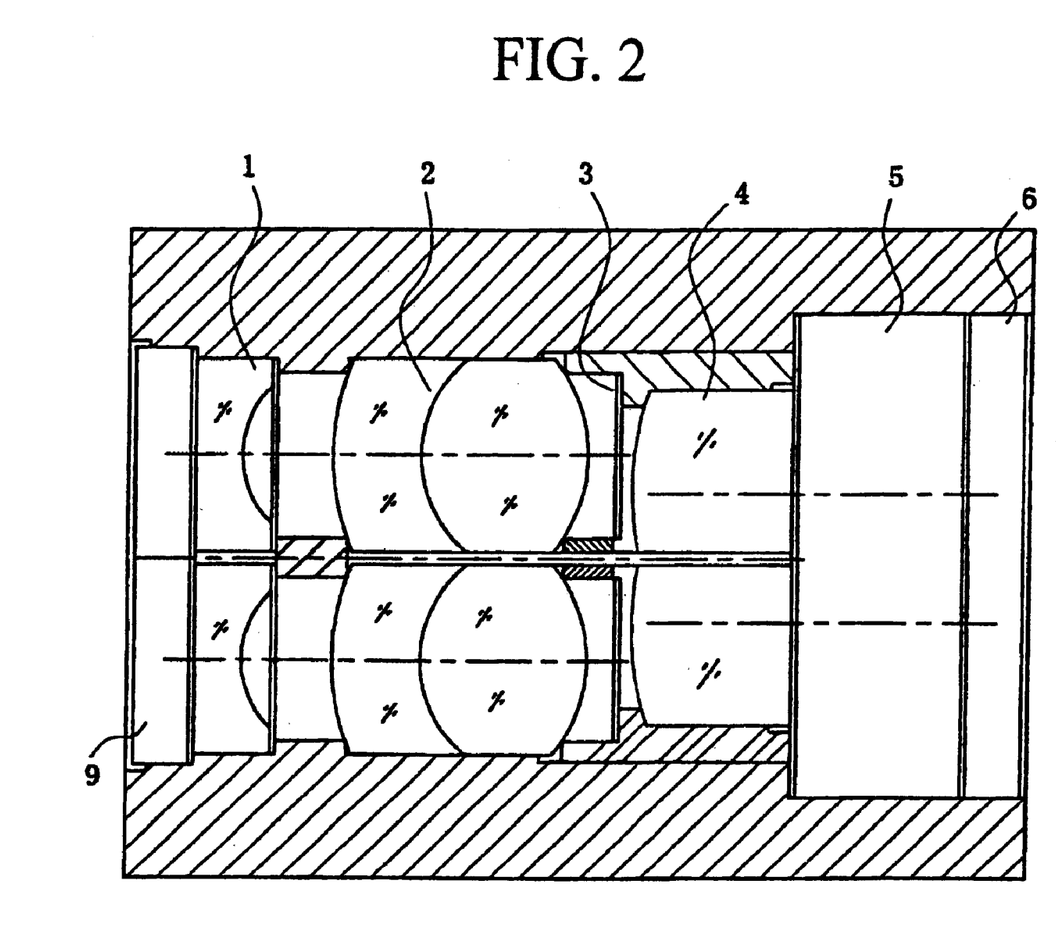
FIG. 2 illustrates a sectional drawing including the frame of an adapter part shown in FIG. 1.

FIG. 2 is a sectional drawing including the frame of an adapter part. The structure is watertight by incorporating a cover glass 9 at its end.

FIGS. 3(a)(b) illustrate an object optical system according to a second example of the present invention. FIG. 3(a) is a top view of the object optical system. FIG. 3(b) is a side view of the object optical system. In this example, the object optical system is different from the object optical system of the first example in that a cover glass 9 and a prism 10 are arranged at the object side for converting a line of sight.

Namely, in order from an object side, the object optical systems consists of a prism 10 for converting the line of sight, a pair of negative lenses 1, a pair of positive-lenses 2, a brightness diaphragm 3 consists of two apertures, a pair of second positive-lenses 4, an infrared cut off filter 5, cover glasses 6, 7 and an image-pick-up device 8.

At the end of prism for converting the line of sight 10, the cover glass 9 that is common for right and left optical systems is arranged. The prism 10 for converting the line of sight also consists of a 90 degree side vision rectangular prism.

This example also has the structure of an end adapter system, wherein the optical object system is detachable from the image-pick-up device 8.

Since the part at the side of the image-pick-up device 8 is common to the object optical system of the first example, direct vision and side vision can be obtained by replacing the adapter of the second example with that of the first example. system of the first example, direct vision and side vision can be obtained by replacing the adapter of the second example with that of the first example.

The value corresponding to each above-mentioned conditional expression and lens data are as follows.

x=0.856 d=1.635
L=10.167
$0.2 \leq x/d=0.52 \leq 0.9$
$0.03L<d=0.16L<2L$
Object distance 10.1672

| | | | |
|---|---|---|---|
| r1 = infinity | d1 = 0.3804 | n1 = 1.88300 | v1 = 40.76 |
| r2 = infinity | d2 = 0.1902 | | |
| r3 = infinity | d3 = 2.2580 | n3 = 1.88300 | v3 = 40.76 |
| r4 = infinity | d4 = 0.1303 | | |
| r5 = infinity | d5 = 0.3804 | n5 = 1.88300 | v5 = 40.78 |
| r6 = 0.8526 | d6 = 0.2092 | | |
| r7 = infinity | d7 = 0.3215 | | |
| r8 = 1.7120 | d8 = 0.4990 | n8 = 1.84666 | v8 = 23.78 |
| r9 = 0.8560 | d9 = 1.1413 | n9 = 1.51633 | v9 = 64.14 |
| r10 = −1.1315 | d10 = 0.7160 | | |
| r11 = infinity(diaphragm) | d11 = 0.0951 | | |
| r12 = 2.0201 | d12 = 0.7630 | n12 = 1.78800 | v12 = 47.37 |
| r13 = infinity | d13 = 0.0285 | | |
| r14 = infinity | d14 = 1.1413 | n14 = 1.51400 | v14 = 75.00 |
| r15 = infinity | d15 = 0.0285 | | |
| r16 = infinity | d16 = 0.3804 | n16 = 1.88300 | v16 = 40.76 |
| r17 = infinity | d17 = 0.1902 | | |
| r18 = infinity | d18 = 0.7609 | n18 = 1.88300 | v18 = 40.76 |
| r19 = infinity | d19 = 0.2853 | n19 = 1.49700 | v19 = 81.61 |
| r20 = infinity | d20 = 0.0285 | | |
| r21 = infinity | | | |

The eccentricity of each convex lens 4=0.39 horizontally.

FIG. 4 illustrates an object optical system according to a third example of the present invention. In this example, the object optical system is different from the object optical system of the first example in that the optic-axial distance of the optical axes is constant before and after the pair of positive-lenses 4, and is narrowed by the convex surfaces, oriented toward the object side, of the pair of positive-lenses 4.

The object optical system consists of a pair of negative lenses 1, a pair of positive-lenses 2, a brightness diaphragm 3, a second pair of positive-lenses 4, an infrared cut off filter 5, and cover glasses 6, 7, an image-pick-up device 8 in order from an object side.

The positive-lenses 4 include a pair of positive lenses which are tilted eccentrically by angle a to each optical axis from the object side to the brightness diaphragm 3, respectively.

This example also has the structure of an end adapter system, wherein the optical object system is detachable from the image-pick-up device 8.

The value corresponding to each above-mentioned conditional expression and lens data are as follows.

x=0.77 d=1.44
L=12.512
$0.2 \leq x/d=0.53 \leq 0.9$
$0.03L<d=0.12L<2L$
Object distance 12.512

| | | | |
|---|---|---|---|
| r1 = infinity | d1 = 0.40004 | n1 = 1.883 | v1 = 40.78 |
| r2 = 1.1009 | d2 = 0.2991 | | |
| r3 = infinity | d3 = 0.4004 | n2 = 1.883 | v2 = 40.78 |
| r4 = 1.2396 | d4 = 0.3815 | | |
| r5 = 1.4434 | d5 = 1.091 | n5 = 1.84666 | v5 = 23.78 |
| r6 = 0.7628 | d6 = 0.9842 | n6 = 1.51633 | v6 = 64.14 |
| r7 = −1.1285 | d7 = 0.05 | | |
| r8 = infinity(diaphragm) | d8 = 0.1001 | | |
| r9 = 1.5541 | d9 = 0.933 | n9 = 1.788 | v9 = 47.37 |
| r10 = 2.7305 | d10 = 0.4665 | n10 = 1.51633 | v10 = 64.14 |
| r11 = 2.5486 | d11 = 0.3003 | | |
| r12 = infinity | d12 = 1.2012 | n12 = 1.514 | v12 = 75.00 |
| r13 = infinity | d13 = 0.03 | | |
| r14 = infinity | d14 = 0.4004 | n14 = 1.883 | v14 = 40.76 |
| r15 = infinity | d15 = 0.2002 | | |
| r16 = infinity | d16 = 0.8008 | n16 = 1.883 | v16 = 40.76 |
| r17 = infinity | d17 = 0.3003 | n17 = 1.497 | v17 = 81.61 |
| r18 = infinity | d18 = 0.03 | | |
| r19 = infinity | | | |

The eccentricity of each convex lens 4 (Angle α of FIG. 4)=10 degrees

FIG. 5 illustrates an object optical system according to a fourth example of the present invention. In this example, the brightness diaphragm 3 consists of two apertures.

Further, the optical system includes a pair of positive-lenses consisting of a pair of convex meniscus lenses 11 with the concave surface oriented toward the object side, a pair of positive lenses 12 with the convex surface oriented to the object side, an infrared cut off filter 6, and cover glasses 6, 7, in order from the brightness diaphragm 3.

Moreover, a parallelogram prism 13 which makes the optical axis behind the brightness diaphragm 3 eccentric is arranged in only one optical system on an object side from the brightness diaphragm 3. Furthermore, in the other optical object system only the parallel plate 14 is arranged so that optical axis is not eccentric behind the brightness diaphragm 3. This is in contrast to the conventional optical system, for example, as shown in FIG. 10, wherein a pair of prism are arranged.

However, the parallelogram prism 13 which makes the optical axis eccentric has a comparatively small eccentricity so a precise prism process in not necessary.

Moreover, although a prism element was used in this example, similar eccentricity may be obtained by arranging the two mirrors facing to each other.

This example also has the structure of an end adapter system, wherein the optical object system is detachable from the image-pick-up device 8.

The value corresponding to each above-mentioned conditional expression and lens data are as follows.

x=0.833 d=1.351
L=10.094
$0.2 \leq x/d = 0.62 \leq 0.9$
0.03L<d=0.13L<2L
Object distance 10.0937

| | | | |
|---|---|---|---|
| r1 = infinity | d1 = 1.0372 | n1 = 1.88300 | v1 = 40.76 |
| r2 = infinity(diaphragm) | d2 = 0.0926 | | |
| r3 = −0.6631 | d3 = 0.9568 | n3 = 1.88300 | v3 = 40.76 |
| r4 = −0.8176 | d4 = 0.0926 | | |
| r5 = 1.6107 | d5 = 0.9260 | n5 = 1.51400 | v5 = 75.00 |
| r6 = infinity | d6 = 0.3704 | n6 = 1.88300 | v6 = 40.76 |
| r7 = infinity | d7 = 0.1852 | | |
| r8 = infinity | d8 = 0.7408 | n8 = 1.88300 | v8 = 40.76 |
| r9 = infinity | d9 = 0.4630 | | |
| r10 = infinity | d10 = 0.0278 | n10 = 1.49700 | v10 = 81.54 |
| r11 = infinity | d11 = 0.0037 | | |
| r12 = infinity | | | |

The eccentricity in the parallelogram prism 13=0.518 horizontally.

In addition, in each Example, x, d, L, and lens data are standardized based on the focal-length f=1. Moreover, r1, r2, . . . express the radius of curvature of each lens surface, cover-glass surface, or prism surface; d1, d2, . . . express the thickness or the air space of each lens, cover glass, or prism; n1, n2, . . . express the refractive indexes of each lens, cover glass, or prism; and v1, v2, . . . express the Abbe number of each lens, cover glass, or prism, respectively.

What is claimed is:

1. An endoscope apparatus which includes an object optical system to conduct measurements or stereoscopic-vision observations, said object optical system comprising:
    a pair of negative lenses;
    a first pair of positive lenses;
    a brightness diaphragm;
    a second pair of positive lenses; and
    an image-pick-up device for forming an object image, said elements being arranged in order from an object side, wherein
    a pair of optical axes are defined by said pair of negative lenses, said first pair of positive lenses and said brightness diaphragm, and
    wherein the lenses of said second pair are arranged inwardly eccentrically with respect to said pair of optical axes.

2. The endoscope apparatus according to claim 1, wherein the following conditional espression is satisfied:

$$0.2 \leq x/d \leq 0.9 \quad (1)$$

wherein x represents an optic-axial distance of said pair of optical axes at said image-pick-up device, and d represents the optic-axial distance of said pair of optical axes at said object side.

3. The endoscope apparatus according to claim 2, wherein the lenses of said second pair are shifted in a direction in which said lenses come closer to each other.

4. The endoscope apparatus according to claim 3, wherein the lenses of said second pair are shifted symmetrically and by the same amount.

5. The endoscope apparatus according to claim 1, wherein said pair of negative lenses, said first pair of positive lenses, said brightness diaphragm and said second pair of positive lenses are in the side of an end adapter, and the adapter is detachable from said image-pick-up device.

6. An endoscope apparatus which includes an object optical system to conduct measurements or stereoscopic-vision observations, said object optical system comprising:
    a pair of negative lenses;
    a first pair of positive lenses;
    a brightness diaphragm;
    a second pair of positive lenses; and
    an image-pick-up device for forming an object image, said elements being arranged in order from an object side, wherein
    a pair of optical axes are defined by said pair of negative lenses, said first pair of positive lenses and said brightness diaphragm,
    wherein the lenses of said second pair are arranged inwardly eccentrically with respect to said pair of optical axes, and
    wherein the following conditional expression is satisfied:

$$0.03L < d < 2L \quad (2)$$

wherein d represents the optic-axial distance of said pair of optical axes at said object side, and L represents the best observation distance of said object optical system.

* * * * *